United States Patent [19]

Dewitt

[11] 4,310,637

[45] Jan. 12, 1982

[54] HIGH IMPACT COMPOSITIONS CONTAINING POLYCYANO NORBORNENES

[75] Inventor: Elmer J. Dewitt, Cuyahoga Falls, Ohio

[73] Assignee: The B. F. Goodrich Company, Akron, Ohio

[21] Appl. No.: 232,610

[22] Filed: Feb. 9, 1981

[51] Int. Cl.³ .............................................. C08L 51/00
[52] U.S. Cl. ...................................... 525/75; 525/76; 525/210
[58] Field of Search ........................... 525/75, 76, 210

[56] References Cited

U.S. PATENT DOCUMENTS 4,132,750  1/1979  Ueshima et al. .................... 525/210

Primary Examiner—J. Ziegler
Attorney, Agent, or Firm—George A. Kap; J. Hughes Powell, Jr.

[57] ABSTRACT

A blend of 100 parts by weight of a polycyano norbornene, such as poly)2-norbornene-5 nitrile); 5 to 15 parts of a halogenated polyolefin, such as chlorinated polyethylene; and 10 to 40 parts of an ABS polymer, such as acrylonitrile-butadiene-styrene resin. This blend, when formed into a rigid structure, has an unexpectedly higher impact strength.

10 Claims, No Drawings

HIGH IMPACT COMPOSITIONS CONTAINING POLYCYANO NORBORNENES

BACKGROUND OF THE INVENTION

Polycyano norbornenes are amorphous thermoplastics that have a glass transition temperature of about 135° C., outstanding oil resistance due to the high nitrile content, and a high heat distortion temperature of about 110° C. They have other desirable properties, such as resistance to hydrocarbon solvents (including aromatics), an excellent barrier to carbon dioxide and oxygen, good tensile strength, and they process easily on roll mills and in injection molding machines.

The main drawbacks of these polymers are their low impact strength which is less than about 0.5 J/cm. Unlike the polyalkyl norbornenes, which can have their impact strength enhanced by the addition of calcium stearate or ethylene-vinylacetate copolymer, it was not possible to improve impact strength of polycyano norbornenes in such a manner. This is surprising in view of the structural similarity of polyalkyl norbornenes and polycyano norbornenes and in view of the fact that the two polymer classes can be prepared by the ring-opening polymerization technique.

It is, therefore, desirable to retain the beneficial properties of the polycyano norbornenes and to improve impact strength thereof.

SUMMARY OF THE INVENTION

This invention relates to thermoplastic compositions which are blends of a polycyano norbornene, a chlorinated polyolefin, and an ABS polymer that show an unexpected improvement in impact strength and melt flow properties. In a preferred embodiment, the compositions comprise 5 to 15 parts chlorinated polyolefin, and 10 to 40 parts ABS resin per 100 parts of a polycyano norbornene, more precisely identified as poly(5-cyanonorbornene-2) or 5-cyano bicyclo[2,2,1]-heptene-2.

DETAILED DESCRIPTION OF THE INVENTION

Success of the compositions described herein in achieving both high impact strength and improved melt flow depends on the presence of three critical components: a polycyano norbornene, chlorinated polyolefin and an ABS resin. Absence of any one of these components from a blend will make it impossible to attain the desired properties. For instance, when a polycyano norbornene resin is melt blended with a chlorinated polyolefin, only a slight Izod impact improvement is realized. Similarly, when a polycyano norbornene resin is combined with an ABS resin, a relatively low Izod impact results. The synergistic effect of a chlorinated polyolefin and an ABS resin when combined with a polycyano norbornene resin is dramatic, as will be demonstrated hereinafter.

It should be noted that both the impact strength and melt flow properties of the compositions claimed herein are improved simultaneously. This is unexpected since these two properties move in opposite directions.

On the basis of 100 parts by weight of a polycyano norbornene, amount of chlorinated polyolefin can vary from 2 to 30 parts, preferably 5 to 15 parts, and amount of an ABS polymer can vary from 5 to 100 parts, preferably 10 to 40 parts.

Suitable polycyano norbornenes have molecular weights below about 25,000, preferably in the range of 10,000 to 20,000. They are prepared from cyano norbornene monomers defined by the following structural formula:

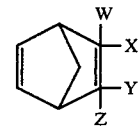

where W, X, Y and Z groups can be hydrogen, nitrile group, substituents containing a nitrile group, alkyl radicals of 1 to 20 carbon atoms, alkenyl radicals of 2 to 20 carbon atoms, aryl radicals of 6 to 20 carbon atoms, and aralkyl radicals of 7 to 20 carbon atoms, provided that at least one of W, X, Y and Z is a nitrile group or a substituent containing a nitrile group. In a preferred embodiment, the groups of W, X, Y and Z are selected from hydrogen, nitrile group, radicals defined herein containing nitrile group, alkyl radicals of 1 to 10 carbon atoms, alkenyl radicals of 2 to 10 carbon atoms, phenyl radical or phenylalkyl radicals of 7 to 12 carbon atoms, provided that at least one but not more than two of W, X, Y and Z groups are nitrile groups or substituents containing the nitrile group. The substituents containing the nitrile group include cyanomethyl, cyanoethyl, cyanopropyl, cyano-n-butyl, cyanoisobutyl, and omega-cyano-n-heptyl radicals. The hydrocarbon radicals preferably contain one to about 10 carbon atoms.

The monomers defined above can be prepared by reacting cyclopentadiene with dienic compounds containing nitrile group by the Diels-Alder reaction. These monomers can also be obtained by reacting dicyclopentadiene with olefinic compounds containing the nitrile group. The olefinic compounds bearing the nitrile group which can be used in the aforesaid reaction include acrylonitrile, methacrylonitrile, α-n-octyl acrylonitrile, vinylidene cyanide, fumaronitrile, maleonitrile, allylcyanide, cinnamonnitrile, and linolonitrile. Specific examples of the cyano norbornene monomers that can be obtained by the Diels-Alder reactions and olefinic reactants described herein include 5-cyano bicyclo[2,2,1]-heptene-2, 5-cyano-5-methyl bicyclo[2,2,1]-heptene-2, 5-cyano-5-n-octyl bicyclo[2,2,1]-heptene-2, 5,5-dicyano bicyclo[2,2,1]-heptene-2, 5,6-dicyano bicyclo[2,2,1]-heptene-2, 5-cyano-6-phenyl bicyclo[2,2,1]-heptene-2, 6-n-2-octenyl bicyclo[2,2,1]-heptene-2, 6-n-pentyl bicyclo[2,2,1]-heptene-2, and mixtures thereof.

The nitrile group and a substituent containing nitrile group can take the endo or exo position. Though the cyano substituted norbornene derivatives consist of two groups of isomers represented by the endo and the exo positions occupied by the groups or substituents, yet said different groups of isomers can be effectively separated from each other by distillation. The endo type of isomer, for example, 5-cyano-bicyclo[2,2,1]-heptene-2 remains solid at room temperature and has a boiling point of 88° C. in an atmosphere reduced to 12 mm Hg. The exo type is a colorless liquid at room temperature, and has a boiling point of 80.5° C. in an atmosphere reduced to 12 mm Hg. Said isomers can be used in a separated or nonseparated state in performing the ring-opening polymerization. It is possible to use a single or two or more types of the above-mentioned cyano substituted norbornene derivatives in preparing polymers thereof.

Polymers of the norbornene derivatives can be prepared by ring-opening polymerization of the various types of norbornene derivatives in the presence or absence of an inert organic solvent using a catalytic system consisting of a mixture of organic aluminum compounds and compounds of tungsten and/or those of molybdenum or a catalytic system consisting of said mixture to which there is added at least one compound selected from the group consisting of water, peroxides, epoxides, organic halides, acetal compounds, alcoholic compounds, phenolic compounds, orthoformic acid esters and orthocarboxylic acid esters.

The ring-opening polymerization is carried out generally at a temperature ranging from −100° C. to +200° C. or preferably −40° C. to +100° C. At a temperature below −100° C., the reaction system does not display desirable polymerization activity with the resultant extremely slow progress of polymerization. In such a case, progress of the polymerization consumes a great deal of time sometimes causing a mixture of the inert organic solvent and monomer to be solidified. Conversely, a temperature above 200° C. fails to provide a good quality of polymer prepared by ring-opening polymerization, and is practically undesirable.

It is preferred to conduct ring-opening polymerization in an inert atmosphere such as argon and nitrogen. If oxygen and moisture are present in the reaction system, then the catalytic compounds, i.e., the organic aluminum compounds and the compounds of tungsten or molybdenum, will be substantially ineffective in promoting reproducible polymerization.

The polymers prepared by ring-opening polymerization of cyano-substituted norbornene derivatives include not only homopolymers of cyano-substituted norbornene derivatives obtained by the above-mentioned process but also copolymers prepared by the ring-opening polymerization of a mixture of the cyano-substituted norbornene derivatives as a main component and other cycloolefinic compounds. Preparation of such polymers can be carried out in the same manner as in producing the homopolymers of said cyano-substituted norbornene derivatives.

When the above mentioned copolymers of cyano-substituted norbornene derivatives are used in producing the resin compositions of this invention, it is preferred that said copolymers be formed by ring-opening polymerization of a mixture containing up to one mol of other cycloolefinic compounds based on one mol of cyano-substituted norbornene derivatives. Where said other cycloolefinic compounds, such as cyclopentene and cyclooctene, are used in excess of one mol, then the resulting resin composition will have a lower surface hardness and softening point.

U.S. Pat. No. 4,132,750 is hereby incorporated by reference for its description of and preparation of the polycyano norbornenes.

Halogenated polyolefins, such as chlorinated polyethylene and chlorinated polypropylene, are well known in the art and their preparation is disclosed in many U.S. Pat. Nos. such as 2,183,556 and 2,890,213. This includes both high pressure and low pressure halogenated polyolefins which can contain 2 to 5 carbon atoms, in the preferred embodiment. The degree of halogenation of the polyolefins suitable for use in this invention can typically range from about 10% to about 50%, preferably 30% to 40%, depending on the number of structural units present in the polymer.

Preferably, polyolefins to be chlorinated are essentially linear polymers containing at least 90 mole percent ethylene in the polymer molecule with the remainder being one or more ethylenically unsaturated comonomers. Examples of useful ethylenically unsaturated comonomers are the nonaromatic hydrocarbon olefins having 3 or more carbon atoms such as propylene, butene-1, 1,7-octadiene; cycloaliphatic olefins such as cyclopentene and 1,5-cyclooctadiene; substituted olefins such as acrylic acid and its esters; conjugated diolefins such as butadiene; alkenyl aromatic compounds such as styrene; and other polymerizable monomers known in the art. The polymers are prepared under the influence of a catalyst system comprising admixtures of strong reducing agents such as triethyl aluminum, and compounds of groups IV-B, V-B and VI-B metals of the Periodic System, such as titanium tetra-chloride, and the like.

The chlorinated low pressure polyethylene, for instance, is produced by chlorinating fine-grained low pressure polyethylene which may have been thermally treated for 5 to 300 minutes at a temperature of from 100° C. to its crystalline melting point, in hydrochloric acid. Chlorination is commenced at 50° to 100° C. and terminated at 120° to 130° C. Chlorinated polyolefins can also be prepared by chlorinating a high density polyethylene, i.e., 0.93 to 0.98 g/cc, and an amount generally less than 10 mol percent of an α-olefin, such as propylene or butene-1, in a solvent or an aqueous suspension. Such chlorinated polyethylene cotains 25 to 45% by weight chlorine.

The ABS resins are a class of resins which are prepared by polymerizing a vinyl aromatic compound, such as styrene, or any suitable alkylated styrene, and an acrylic nitrile, such as acrylonitrile, in the presence of a conjugated diene polymer, such as polybutadiene. The ABS resins are generally a mixture of rubber particles dispersed in styrene-acrylonitrile matrix. At least a part of the styrene and acrylonitrile is usually polymerized in the presence of the elastomeric polybutadiene backbone. These graft polymers are prepared from mixtures of other acrylic nitriles, such as methacrylonitrile, chloroacrylonitrile, and ethacrylonitrile, and other vinyl aromatic compounds, such as methyl styrene and vinyl toluene, with other diolefin polymers, such as polychloroprene, polyisoprene, and elastomeric butadiene copolymers, examples of which are butadiene-styrene, butadiene-acrylonitrile, and butadiene-alkyl acrylates. Alkyl methacrylates, such as methyl methacrylate, can be used in addition to or in place of acrylonitrile and styrene, if desired.

The vinyl aromatic compound can contain 8 to 12 carbon atoms, but preferably 8 to 9. Acrylic nitrile is defined by the following formula:

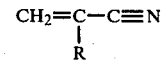

where R is selected from hydrogen, halogens, alkyl radicals of 1 to 8 carbon atoms, and aryl radicals; preferably, R is selected from hydrogen, chlorine, and alkyl radicals of 1 to 2 carbon atoms. The conjugated diene monomer is defined by the formula

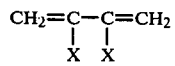

where X's are individually selected from hydrogen, halogens, alkyl radicals of 1 to 5 carbon atoms, and aryl radicals; preferably, X's are individually selected from hydrogen, chlorine, and alkyl radicals of 1 to 3 carbon atoms. The conjugated diene monomer can be polymerized and then graft polymerized with the vinyl aromatic compound and the acrylic nitrile monomer to form the ABS resin, as already noted.

Proportions of monomers used to prepare ABS resins can vary from about 40 to 90 parts by weight of combined acrylic nitrile and vinyl aromatic compound with about 60 to 10 parts of the diene elastomer. On the basis of the three components, acrylic nitrile is present in amount of 10 to 40 parts, vinyl aromatic compound in amount of 30 to 80 parts, and diene in amount of 10 to 60 parts.

Blends of a polycyano norbornene, a chlorinated polyolefin and an ABS polymer are prepared by working the polycyano norbornene resin on a mill heated to about 380° F. until it is melted. At this point, the ABS resin is slowly worked in and melted followed by the chlorinated polyolefin. This blending operation takes about 5 minutes for batches of about 0.2–0.5 pound size. These blends can also be melt-mixed in larger equipment, such as the Banbury mixers and extruders.

The blends disclosed herein have applications which exploit their high heat distortion temperature and high impact strength. In particular, these blends, in the form of hardened materials, can be used in computer, television and radio housings, and other sundry applications.

A number of examples are presented below to demonstrate efficacy of the blends disclosed therein in comparison with the resins themselves and binary blends thereof. The test used to determine heat distortion temperature was ASTM D-648-56 and the notched Izod impact test was ASTM D-256-56. The melt flow test was carried out in a ½-inch barrel by applying a weight of 500 pounds on a 4-gram sample and forcing it through a die with a diameter of 0.0459 inch and a length of 0.3260 inch. The sample temperature was 190° C. and it was preheated for 6 minutes.

EXAMPLES 1 to 5

Five samples were prepared to demonstrate synergism of the compositions disclosed herein with respect to impact strength. The samples were prepared by blending ingredients identified in Table I, below, and then testing the samples for notched Izod impact strength, HDT and melt flow. The formulations in parts by weight and test results are given in table below:

TABLE I

| Ingredients | Samples | | | | |
|---|---|---|---|---|---|
| | 1 | 2 | 3 | 4 | 5 |
| PN Resin | 90 | 75 | 50 | 80 | 75 |
| ABS Resin | — | 25 | 50 | 15 | 25 |
| Chlorinated PE | 10 | — | — | 10 | 10 |
| Lubricant B | 2 | 2 | 2 | 2 | 2 |
| HDT, °C. @ 264 psi | 101 | 101 | 98 | 101 | 100 |
| Notched Izod, J/cm | 1.2 | 1.1 | 2.3 | 8.5 | 8.4 |
| Melt Flow, g/10 min. | 45 | 30 | 20 | 61 | 57 |

The PN resin in the table, above, is poly(2-norbornene-5-nitrile) which had DSV of 0.51 measured in methylene chloride (0.1 g/100 ml), notched Izod of 0.81 J/cm, heat distortion temperature of 111° to 113° C., and a glass transition temperature of 134° C. This data was obtained on compression molded samples. The ABS resin is composed of 30% polybutadiene and 70% styrene-acrylonitrile where the SAN is 68% styreene and 32% acrylonitrile. Chlorinated polyethylene rubber contained 36% chlorine and the lubricant is oxidized polyethylene homopolymer.

The dramatic synergism of the compositions described herein is clearly evident from the impact strength and melt flow results given in Table I, above. Sample 1 was prepared with 90 parts of the polycyano norbornene resin and 10 parts of chlorinated polyethylene but without the ABS resin. Bearing in mind that Izod impact for the polycyano norbornene resin is only 0.81 J/cm, there was some improvement in the impact strength of 1.2 for sample 1. Izod impact for sample 2 was 1.1 J/cm, which was composed of the polycyano norbornene resin and the ABS resin but without chlorinated polyethylene. Sample 3 was similar to sample 2 but amount of the ABS resin was increased to 50 parts at the expense of the polycyano resin. Izod impact of sample 3 was 2.3 J/cm, or about double that for samples 1 and 2. Sample 4 had the combination of the three critical ingredients, i.e., the polycyano resin, the ABS resin, and the chlorinated polyethylene. Izod impact of samples 4 and 5 was an incredible 8.5 and 8.4 J/cm, respectively, which is several times that of samples 1, 2 and 3.

It is also important to note that melt flow for samples 4 and 5 was high compared to the other samples. The fact that impact strength increased with an increase in melt flow is unexpected in itself. Generally, improvement in these two properties is not in tandem, i.e., if one increases the other decreases. In this instance, it is surprising to see both impact strength and melt flow show improvement.

With HDT of about 100° C., it is apparent that blends of a polycyano norbornene, a chlorinated polyolefin, and a nitrile polymer would make good engineering thermoplastics. This is also surprising since the polycyano norbornenes are relatively brittle thermoplastics.

EXAMPLES 6 to 14

Additional samples were prepared by blending the ingredients noted in Table II, below, and then testing the samples for melt flow, heat distortion temperature, and notched impact strength. The ingredients are stated in parts by weight. Results of the tests are given in Table II, below:

TABLE II

| Ingredients | Sample No. | | | | | | | | |
|---|---|---|---|---|---|---|---|---|---|
| | 6 | 7 | 8 | 9 | 10 | 11 | 12 | 13 | 14 |
| ABS-A | — | 15 | 50 | 25 | — | 25 | — | 15 | 15 |
| ABS-B | — | — | — | — | 25 | — | — | — | — |
| PN Resin | 90 | 80 | 50 | 75 | 75 | 75 | 75 | 50 | 60 |
| Poly(Methyl Methacrylate) | — | — | — | — | — | — | 25 | 50 | 40 |
| MBS | — | — | — | — | — | — | — | — | 10 |
| Chlorinated PE | 10 | 10 | — | — | — | 10 | 10 | 10 | — |
| Lubricant A | 1 | 1 | 1 | 1 | 1 | 1 | 1 | 1 | 1 |
| Lubricant B | 1 | 1 | 1 | 1 | 1 | 1 | 1 | 1 | 1 |
| Mill Temp., °F. | 380 | 380 | 380–340 | 360 | 360 | 360 | 360 | 360 | 360 |
| Molding Temp., °F. | 360 | 360 | 360 | 360 | 360 | 360 | 360 | 360 | 360 |
| Melt Flow, g/10 min. | 45 | 61 | 20 | 30 | 51 | 57 | 39 | 40 | 26 |
| HDT, °C. | 101 | 101 | 98 | 101 | 97 | 100 | 95 | 85 | 81 |
| Izod Impact, J/cm | 1.2 | 8.5 | 2.3 | 1.1 | 0.7 | 8.4 | 0.9 | 1.2 | 1.6 |

In the above table, ABS-A is a high impact Abson 89005-021 resin which is composed of 30% polybutadiene and 70% styrene-acrylonitrile where the SAN is 68% styrene and 32% acrylonitrile. ABS-B is another acrylonitrile-butadiene-styrene resin similar to the Abson resin. The PN resin is poly(2-norbornene-5-nitrile) which has a molecular weight of less than 25,000, notched Izod impact strength of about 0.8 J/cm, heat distortion temperature of about 110° C. to 115° C., and a glass transition temperature of 135° C. The data on the PN resin is based on injection molded samples. Poly(methyl methacrylate) in the blends identified in the above table is an impact modified grade. Chlorinated polyethylene contains 36% chlorine by weight. Lubricant A is Microthene 512, a low molecular weight polyethylene whereas Lubricant B is oxidized polyethylene homopolymer.

The results in Table II indicate synergism of the compositions with respect to Izod impact strength. It should be apparent that in terms of notched Izod impact strength, the combination of a polycyano norbornene, a chlorinated polyolefin, and a nitrile polymer can produce unexpected results.

I claim:

1. Thermoplastic composition having both improved impact strength and melt flow comprising 2 to 30 parts by weight of a halogenated polyolefin; 5 to 100 parts by weight of an ABS resin that is a polymerization product of a vinyl aromatic compound, an acrylic nitrile, and a conjugated diene; and 100 parts by weight of a polycyano norbornene.

2. Composition of claim 1 wherein the polycyano norbornene is a polymerization product of cyano norbornene monomers defined by the following structural formula:

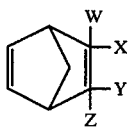

where W, X, Y and Z groups are selected from hydrogen, nitrile group or substituents containing a nitrile group, alkyl radicals of 1 to 20 carbon atoms, alkenyl radicals of 2 to 20 carbon atoms, aryl radicals of 6 to 20 carbon atoms, and aralkyl radicals of 7 to 20 carbon atoms, provided that at least one of W, X, Y and Z groups is nitrile group or a substituent containing nitrile group.

3. Composition of claim 2 where each W, X, Y and Z group in the formula for the cyano norbornene monomers is selected from hydrogen, nitrile group, radicals defined herein containing nitrile group, an alkyl radical of 1 to 10 carbon atoms, an alkenyl radical of 2 to 10 carbon atoms, phenyl radical, or a phenylalkyl radical of 7 to 12 carbon atoms, provided that at least one but not more than two of W, X, Y and Z groups are nitrile groups or radicals defined herein containing nitrile group; the vinyl aromatic compound contains 8 to 12 carbon atoms; the acrylic nitrile is defined by the formula

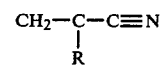

where R is selected from hydrogen, halogens, alkyl radicals of 1 to 8 carbon atoms, and aryl radicals; and the diene is defined by the formula

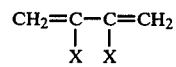

where each X is individually selected from hydrogen, halogens, alkyl radicals of 1 to 5 carbon atoms, and aryl radicals.

4. Composition of claim 3 wherein the vinyl aromatic compound contains 8 to 9 carbon atoms; R in the formula for the acrylic nitrile is selected from hydrogen, chlorine, and alkyl radicals of 1 to 2 carbon atoms; and each X in the formula for the diene is selected from hydrogen, chlorine, and alkyl radicals of 1 to 3 carbon atoms; based on the three components in the ABS resin, amounts of each are 30 to 80 parts vinyl aromatic compound, 10 to 40 parts acrylic nitrile, and 10 to 60 parts of the diene.

5. Composition of claim 2 wherein the ABS resin is a polymerization product of the diene selected from butadiene, chloroprene, isoprene, and mixtures thereof; acrylic nitrile selected from acrylonitrile, chloroacrylonitrile, methacrylonitrile, ethacrylonitrile, and mixtures thereof; and the vinyl aromatic compound selected from styrene and methyl styrene; and the halogenated polyolefin is prepared from olefins containing 2 to 5 carbon atoms.

6. Composition of claim 5 wherein the ABS resin is a graft copolymer of acrylonitrile-butadiene-styrene in the proportion of about 40 to 90 parts by weight of combined acrylonitrile and styrene with about 60 to 100 parts by weight of the butadiene elastomer.

7. Composition of claim 6 wherein the ABS resin is prepared by polymerizing acrylonitrile and styrene in presence of polybutadiene.

8. Composition of claim 5 wherein the halogenated polyolefin is selected from chlorinated polyethylene and chlorinated polypropylene chlorinated to the extent of about 30 to 40 weight percent; amount of the halogenated polyolefin is 5 to 15 parts and amount of the ABS resin is 10 to 40 parts.

9. Composition of claim 8 wherein the cyano norbornene monomers are selected from 5-cyano bicyclo[2,2,1]-heptene-2, 5-cyano-5-methyl bicyclo[2,2,1]-heptene-2, 5-cyano-5-n-octyl bicyclo[2,2,1]-heptene-2, 5,5-dicyano bicyclo[2,2,1]-heptene-2, 5,6-dicyano bicyclo[2,2,1]-heptene-2, 5-cyano-6-phenyl bicyclo[2,2,1]-heptene-2, 6-n-2-octenyl bicyclo[2,2,1]-heptene-2, 6-n-pentyl bicyclo[2,2,1]-heptene-2, and mixtures thereof.

10. Composition of claim 9 wherein the polycyano norbornene has molecular weight of less than 25,000, notched Izod impact strength of about 0.8 J/cm, heat distortion of about 110° C. to 115° C., and glass transition temperature of about 135° C.; and the halogenated polyolefin is chlorinated polyethylene.

* * * * *